Figure 1:
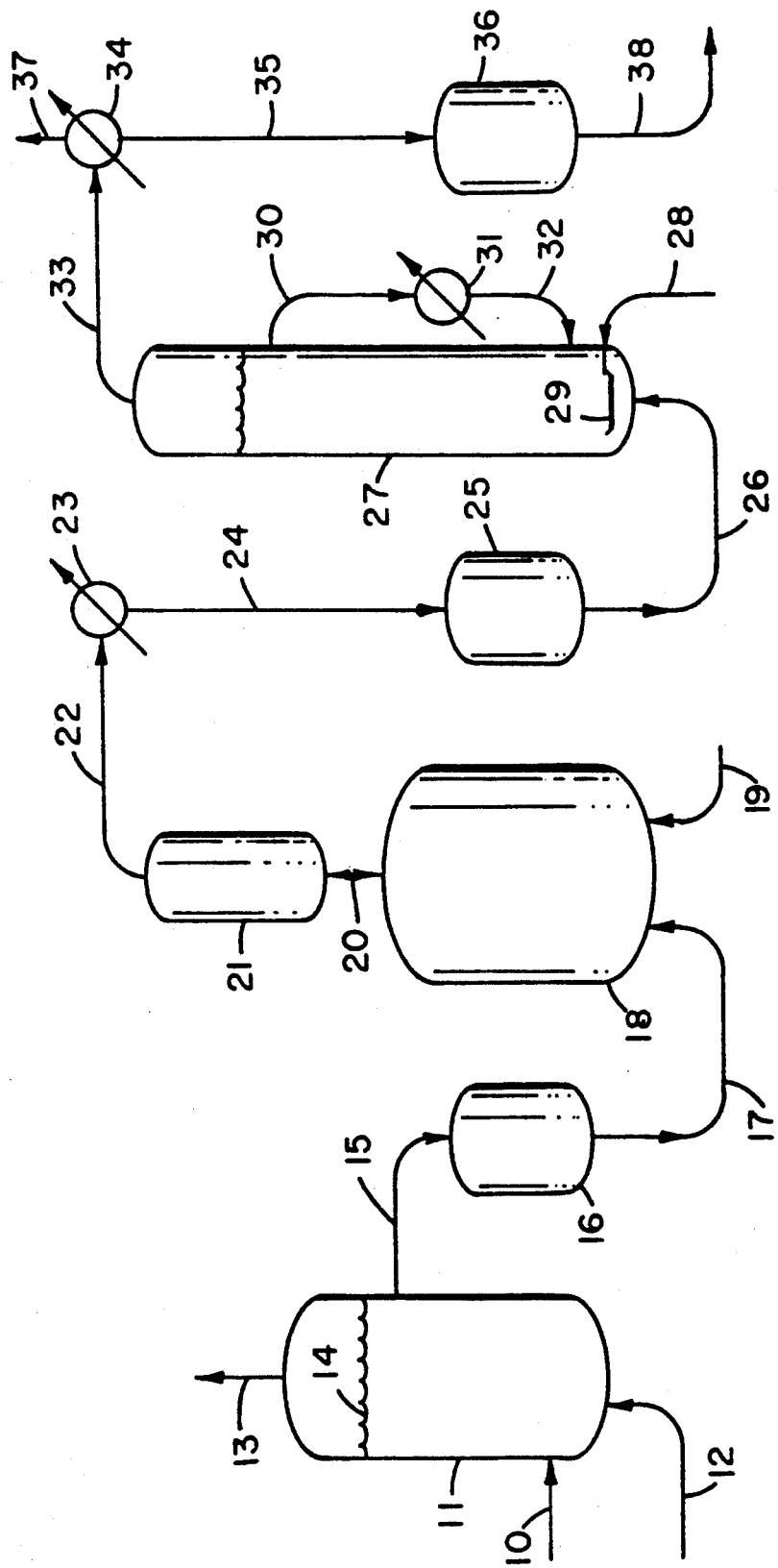

United States Patent [19]

Fillers et al.

[11] Patent Number: 5,175,362
[45] Date of Patent: Dec. 29, 1992

[54] RECOVERY OF ACETYL VALUES FROM ETHYLIDENE DIACETATE

[75] Inventors: Carl F. Fillers, Greeneville, Tenn.; Eric D. Middlemas, Nickelsville, Va.; Hugh M. Thompson, Jr., Johnson CIty, Tenn.; Jerry A. Barron, Gray, Tenn.; William T. Brown, Jonesborough, Tenn.

[73] Assignee: Eastman Kodak Company, Rochester, N.Y.

[21] Appl. No.: 706,662

[22] Filed: May 29, 1991

[51] Int. Cl.$^5$ .................. C07C 53/08; C07C 51/42
[52] U.S. Cl. .................... 562/607; 562/608
[58] Field of Search .................... 562/607, 608

[56] References Cited

U.S. PATENT DOCUMENTS

| | | | |
|---|---|---|---|
| 3,639,472 | 2/1972 | Sennewald et al. | 260/541 |
| 3,927,078 | 12/1975 | Lapporte et al. | 260/494 |
| 4,046,807 | 9/1977 | Kuckertz | 260/549 |
| 4,356,328 | 10/1982 | Moy | 568/484 |
| 4,374,070 | 2/1983 | Larkins et al. | 260/549 |
| 4,559,183 | 12/1985 | Hewlett | 260/546 |
| 4,898,644 | 2/1990 | Van Horn | 203/15 |

FOREIGN PATENT DOCUMENTS

| | | | |
|---|---|---|---|
| 0102835 | 6/1982 | Japan | 562/607 |
| 0197708 | 10/1977 | U.S.S.R. | 562/607 |

Primary Examiner—Josä/e/ G. Dees
Assistant Examiner—Porfirio Nazario
Attorney, Agent, or Firm—J. Frederick Thomsen; William P. Heath, Jr.

[57] ABSTRACT

Disclosed is a process for the recovery of acetyl values from an ethylidene diacetate stream obtained from an acetic anhydride production system. The process comprises hydrolyzing ethylidene diacetate in a liquid phase, hydrolysis zone containing a non-volatile, acidic catalyst and maintained under boiling conditions to obtain a mixture of acetaldehyde, acetic acid and water and then oxidizing the mixture in a liquid phase, oxidation zone containing a cobalt oxidation catalyst to obtain a mixture of acetic acid and water. The process optionally includes a means for reducing substantially the concentration of iodine in the EDA used in the process.

5 Claims, 1 Drawing Sheet

RECOVERY OF ACETYL VALUES FROM ETHYLIDENE DIACETATE

This invention pertains to a process for the recovery of acetyl values from ethylidene diacetate (EDA) wherein EDA is subjected to an acid-catalyzed hydrolysis under boiling conditions to produce a vapor stream comprising acetaldehyde and acetic acid. The vapor stream is then catalytically oxidized to produce an acetic acid vapor stream.

The preparation of acetic anhydride by contacting a mixture comprising methyl iodide and methyl acetate and/or dimethyl ether with carbon monoxide in the presence of a rhodium catalyst has been reported extensively in the patent literature. See, for example, U.S. Pat. Nos. 3,927,078, 4,046,807, 4,374,070 and 4,559,183 and European Patents 8396 and 87,870. It is known, e.g., from U.S. Pat. No. 4,374,070, that the inclusion of a minor amount of hydrogen in the carbon monoxide feed gas results in the formation of EDA. Although the amount of EDA formed per unit of acetic anhydride is low, the amount of EDA produced in a multi-million kilogram per year acetic anhydride plant is substantial. The crude or partially-refined product obtained from such acetic anhydride processes typically comprises a mixture of acetic anhydride, acetic acid and EDA as a result of the use of acetic acid as a process solvent and/or the co production of acetic acid by including methanol and/or water in the feed to the carbonylation reactor.

EDA is a useful chemical intermediate for the production of vinyl acetate, e.g., according to the process described in British Patent 2,013,184. However, the volume of EDA produced as a by-product in large acetic anhydride production systems is not sufficient for the investment required to purify the EDA and convert it to vinyl acetate. Thus, the EDA fraction of the crude product of acetic anhydride processes must be disposed, for example, by incineration.

We have developed a process whereby EDA may be converted to valuable acetyl values by first hydrolyzing the EDA under boiling conditions to produce a vapor stream comprising acetaldehyde and acetic acid and then catalytically oxidizing the vapor stream to produce an a second vapor stream comprising acetic acid and water. Our invention therefore comprises the steps of:

(1) feeding ethylidene diacetate and water to a liquid phase, hydrolysis Zone containing a non-volatile, acidic catalyst and maintained under boiling conditions;

(2) removing from the hydrolysis zone a vapor comprising acetaldehyde, acetic acid and water;

(3) feeding the acetaldehyde, acetic acid and water from step (2) to a liquid phase, oxidation zone containing a cobalt oxidation catalyst; and (4) removing from the oxidation zone a vapor comprising acetic acid and water.

The process provides a means for the substantially quantitative conversion of EDA to acetic acid without loss of acetaldehyde due to its dimerization, trimerization or polymerization, e.g., to produce crotonaldehyde or paraldehyde.

U.S. Pat. No. 3,639,472 discloses the hydrolysis of vinyl acetate using a catalytic amount of a mixture of an organic sulfonic or phosphonic acid and a mercury salt thereof. According to this patent, the feedstock used consists of a mixture of acetic acid, 15 to 40 weight percent vinyl acetate and water and the hydrolysis gives a vinyl acetate conversion of 92 percent or less even though a substantial quantity of sulfonic acid and mercury sulfonate is employed. U.S. Pat. No. 4,356,328 discloses a process for the preparation of acetaldehyde wherein acetic anhydride is hydrogenated in the vapor phase and in the presence of a supported, Group VIII metal catalyst.

The accompanying FIGURE is a process flow diagram illustrating a system embodying the principles of the present invention, including preferred embodiments thereof. It is possible, of course, that the acetyl recovery process may be operated without the purification feature and/or by modifying the specific processes illustrated by the FIGURE.

The hydrolysis zone of the process of the present invention comprises a reaction vessel provided with ports for feeding EDA and water and removing a vapor comprising acetaldehyde, acetic acid and water. To prevent or minimize the presence of EDA or catalyst in the vapor effluent, the hydrolysis zone preferably includes an entrainment separator through which the gaseous effluent passes prior to the oxidation step. The acid catalyst used in our process may be selected from sulfuric acid and organic, sulfonic acids including acidic, ion-exchange resins such as sulfo substituted polymers of styrene and divinyl benzene, e.g., Amberlyst 15 and Amberlite 200 acidic, ion-exchange resins. The organic, sulfonic acids, especially the alkylsulfonic acids, e.g., alkylsulfonic acids having 1 to 4 carbon atoms, are preferred since sulfuric acid and the acidic ion-exchange resins tend to decompose resulting in the presence of sulfur compounds in the effluent from the hydrolysis zone. The catalytically-effective amount of the acidic catalyst may vary significantly depending, for example, on the particular catalyst used and the residence or hold-up time at which the hydrolysis zone is operated. Thus, catalyst concentrations may vary from about 0.05 to 10 weight percent, based on the weight of the liquid phase of the hydrolysis zone, with concentrations of about 0.3 to 1 weight percent being preferred.

In the operation of our process, water and EDA are fed to the hydrolysis zone at rates which maintain a water:EDA molar feed ratio of at least 1:1. As will be apparent to those skilled in the art, sufficient water is used to assure essentially complete hydrolysis of the EDA at reasonable EDA feed rates but some minimum amount of water is fed to minimize the amount of water which is removed from the ultimate acetic acid/water product provided by the process. Therefore, the water:EDA mole ratio within the liquid phase of the hydrolysis zone normally is about 1:1 to 3:1 with a range of about 1.2:1 to 1.5:1 being preferred.

The liquid phase of the hydrolysis zone is maintained at a temperature within the range of about 110° to 130° C. to provide a boiling hydrolysis mixture. At ambient pressure, the temperature of the liquid phase is approximately 113° to 115° C. The boiling conditions within the hydrolysis zone results in the vaporization and removal of acetaldehyde substantially at the rate at which it is formed. Any significant contact time between the acetaldehyde and the acidic hydrolysis medium results in the conversion of a substantial amount of the acetaldehyde to condensation products, oligomers and/or polymers.

The EDA material used in the process of the present invention may comprise about 80 to 100 weight percent EDA with the remainder being acetic acid and acetic anhydride. The EDA-containing stream recovered from the acetic anhydride production system may require a pre-hydrolysis treatment such as a distillation to remove any essentially non-volatile process tars present.

The composition of the vapor stream removed from the hydrolysis zone can vary significantly depending on the amounts of water and acetic acid and/or acetic anhydride fed to the hydrolysis zone. Typically the composition of the vapor stream is about 20 to 27 weight percent acetaldehyde, 70 to 76 weight percent acetic acid and 4 to 7 weight percent water. Normally, this stream is condensed and collected in an oxidizer feed tank prior to the oxidation step.

The oxidation zone comprises an oxidation vessel having means for providing a vigorously agitated, liquid oxidation medium. The oxidation vessel may be a stirred reactor but preferably is a columnar oxidizer to which an oxygen-containing gas such as air, oxygen-enriched air or oxygen is fed at or near the bottom by means of a gas sparging device to provide vigorous agitation. Contact between the acetaldehyde and the oxygen-containing gas and catalyst may be enhanced further by the presence of a circulating loop through which oxidizer medium is removed from the upper section, and returned at the lower section, of the oxidizer. The circulating loop may include a heat exchanger to remove heat from the oxidation zone.

The oxidation is carried out at elevated temperatures and pressures in the presence of a cobalt catalyst wherein the concentration of [Co] is at least 0.18 weight percent based on the liquid phase within the oxidation zone. Typically, the catalytically-effective amount of cobalt in the liquid oxidation medium comprising primarily acetic acid and water is in the range of about 0.18 to 5.0 weight percent [Co]. The oxidation conditions of temperature and pressure usually are within about 100° to 150° C. and about 2.4 to 4.5 bar (absolute).

The acetic acid:water ratio of the oxidizer vapor effluent may vary from about 10:1 to 4:1, depending primarily on the materials fed and feed rates used in the hydrolysis zone. The acetic acid and water may be condensed and most of the water removed according to known means to produce a grade of acetic acid for use in the chemical process industry. Alternatively, the aqueous acetic acid obtained from the oxidation zone may be used as a feedstock in the methyl acetate manufacturing process described in U.S. Pat. No. 4,435,595.

The EDA material used in the acetyl recovery process described herein usually is contaminated with iodine e.g., 50 ppm or more iodine, typically from 100 to 1500 ppm iodine, calculated as [I], primarily in the form of iodoacetic acid, due to the use of an iodine compound or compounds in the acetic anhydride manufacturing system described hereinabove. When the iodine-containing, EDA material is fed to the hydrolysis zone, the iodine compound or compounds in the feed are vaporized substantially unchanged and are a component of the oxidizer feed.

It has been discovered that such iodine compound or compounds, e.g., iodoacetic acid, are converted in the oxidation zone into one or more iodine compounds having a boiling point substantially lower than the temperature at which the acetic acid/water oxidation product is condensed. As a result, the iodine concentration of the condensed acetic acid/water product is reduced substantially, e.g., from 80 to 90 weight percent, relative to the iodine content of the feed to the oxidation zone.

Alternatively, the acetyl recovery process of the present invention may be operated in conjunction or combination with an iodine removal process comprising the steps of:

(i) contacting in a purification zone a mixture comprising EDA, acetic anhydride, acetic acid and iodine, e.g., 50 ppm or greater iodine, usually 100 to 1500 ppm iodine, with aqueous hydrogen peroxide at a temperature of 140° to 160° C.; and (ii) removing from the purification zone
   (a) a vapor phase comprising water, acetic acid and iodine-containing compounds, primarily methyl iodide; and
   (b) a liquid phase comprising EDA containing about 15 to 100 ppm iodine.

The benefits provided by the iodine removal process include reduced corrosion of the hydrolysis/oxidation equipment, a reduction in the amount of iodine present in the ultimate acetic acid product and/or avoiding any possible adverse effects iodine may have on the hydrolysis and/or oxidation catalysts.

The iodine-contaminated EDA material fed to the purification zone comprises about 80 to 100 weight percent EDA, about 0 to 5 weight percent acetic acid and 0 to 10 weight percent acetic anhydride. The water of the aqueous hydrogen peroxide will convert part of the acetic anhydride to acetic acid which is removed as a component of the vapor effluent from the purification zone. Typically, about 90 to 95 weight percent of the iodine contained in the EDA material fed to step (i) is contained in the step (ii)(a) vapor phase removed from the purification zone.

The purification process is carried out by feeding the above described EDA material and aqueous hydrogen peroxide to an agitated vessel from which the gas and liquid phase are removed. The hydrogen peroxide which may be used comprises aqueous hydrogen peroxide having a peroxide content of 3 to 70 weight percent. For economic and safety reasons, the aqueous hydrogen peroxide most suitable has a hydrogen peroxide content of about 30 to 70 weight percent. The amount of peroxide required to achieve a substantial reduction in the amount of iodine present in the EDA can vary depending on the iodine concentration of the EDA material. In general, the amount of aqueous hydrogen peroxide solution used should be about 1 to 10% of the weight of the EDA feed material. The preferred amount of peroxide solution fed to the purification zone is in the range of about 3 to 6% of the weight of the EDA material fed.

Referring to the accompanying FIGURE, a mixture comprising a major amount of EDA and minor amounts of acetic anhydride, acetic acid and iodine-containing compounds is fed by conduit 10 to iodine removal vessel 11 at or near the bottom of the vessel. Aqueous hydrogen peroxide solution is fed via conduit 12, also at or near the bottom of vessel 11 which typically is provided with agitation means (not shown). The feed rates to and the volume of vessel 11 provide a residence or hold-up time of about 0.5 to 3.0 hours. The contents of vessel 11 are maintained at a temperature of about 140° to 160° C. by a reboiler (not shown) to provide a vapor effluent which is removed from vessel 11 by means of conduit 13. Most, e.g., at least 90 to 95 weight percent, of the iodine fed to vessel 11 is removed in the vapor effluent along with water, acetic acid and a minor amount of EDA.

A liquid effluent comprising EDA is removed from vessel 11 below liquid level 14 by means of conduit 15 and collected in EDA tank 16 from which the liquid is fed by conduit 17 to hydrolysis vessel 18 which is provided with means for agitation (not shown). Water is fed by line 19 through which the non-volatile, acidic catalyst may also be fed as necessary to provide the desired concentration of catalyst within vessel 18. The temperature of the contents of vessel 18 are maintained at a temperature of about 110° to 130° C. to maintain boiling conditions. Typical residence times within hydrolysis vessel 18 range from about 0.2 to 1 hour. The acetaldehyde formed in the hydrolysis vessel is vaporized and removed from the liquid phase at substantially the rate at which it is formed to prevent formation of acetaldehyde oligomers and polymers. For example, acetaldehyde is not detected by gas chromatograph analysis of the liquid phase of the hydrolysis zone.

A vapor effluent passes from hydrolysis vessel 18 through conduit 20 to entrainment separator 21 which is provided with heat exchanger means (not shown) to prevent entrained EDA and catalyst from exiting the hydrolysis zone with the acetaldehyde and acetic acid. Entrainment separator 21 is equipped with 5 to 10 sieve trays to provide efficient collection and return of EDA and catalyst to vessel 18 through conduit 20. A mixture consisting essentially of acetaldehyde, acetic acid and water is removed from the top of entrainment separator 21 by line 22, condensed in heat exchanger 23 and the condensate is fed by line 24 to oxidizer feed tank 25.

The mixture of acetaldehyde, acetic acid and water is fed by conduit 26 to oxidizer 27 wherein the acetaldehyde is oxidized to acetic acid at elevated temperature and pressure in the presence of a cobalt catalyst by means of an oxygen-containing gas fed by line 28 and distributed throughout the liquid phase by means of gas sparger 29. Oxidation mixture may be removed near the top of the of the liquid phase by conduit 30 passed through heat exchanger 31 to remove heat generated by the exothermic oxidation reaction and returned to the lower section of the oxidizer by conduit 32. The combination of the air fed by gas sparger 29 and the recirculating loop comprising lines 30 and 32 provides vigorous agitation resulting in good contact between the acetaldehyde, cobalt catalyst and oxygen-containing gas.

Finally, a vapor effluent consisting essentially of acetic acid and water is removed from oxidizer 27 by line 33, condensed in heat exchanger 34 and the condensed product is fed by conduit 35 to product tank 36. Non-condensible gases are removed from heat exchanger 34 via line 37. The water-containing acetic acid is transferred by line 38 to other chemical processing units wherein substantially all of the water is removed or the aqueous acetic acid is used as a feedstock.

Our invention is further illustrated by the following example wherein parts are given by weight and percentages are by weight based on the total weight of the mixtures specified. The EDA-containing mixture used in the example was derived from an EDA-rich stream obtained from the acetic anhydride production system described in U.S. Pat. No. 4,374,070 which was distilled to remove non-volatile process tars.

A mixture containing 0 to 100% EDA, 0 to 5% acetic acid, 0 to 10% acetic anhydride and 100 to 1500 ppm iodine was fed to the lower section of iodine removal vessel 11 at a rate of 340 parts hour through conduit 10. 35% Aqueous hydrogen peroxide was fed to the vessel by means of conduit 12 at 10 to 25 parts per hour. A temperature of 145° to 150° C. was maintained within vessel 11 which provided a residence time of 1 hour. A vapor stream containing 45 to 50% water, 35 to 45% acetic acid, 10 to 18% EDA and 300 to 2700 ppm methyl iodide was removed from vessel 11 at a rate of 11 to 24 parts per hour.

A liquid stream of EDA containing 15 to 100 ppm iodine was removed from the upper section of vessel 11 and fed via conduits 15 and 17 and tank 16 to the bottom section of hydrolysis vessel 18 at a rate of 430 parts per hour. Water was fed to the bottom section of the hydrolysis vessel at a 70 parts per hour. The EDA was hydrolyzed in vessel 18 at 113° to 125° C. and ambient pressure in the presence of 0.5% methanesulfonic acid. The vapor effluent from hydrolysis vessel 18 was fed through conduit 20 to entrainment separator 21 for recovery of entrained EDA and catalyst. The vapor removed from the hydrolysis zone by line 22 and condensed by heat exchanger 23 had an average composition of 20-27% acetaldehyde, 70 to 76% acetic acid and 4 to 7% water.

The condensed material was fed through line 26 at a rate of 160 parts per hour to the bottom of oxidizer 27 to which air was also fed by means of line 28 and gas sparger 29. The temperature and pressure within the oxidizer were maintained at approximately 130° C. and 3.08 bar absolute and the concentration of cobalt [Co] in the liquid oxidation mixture was approximately 3000 ppm. Recirculating lines 30 and 32 and heat exchanger 31 were not used in the procedure of this example. A vapor effluent was removed from the oxidizer via line 33, condensed in heat exchanger 34 and the condensed product was fed to tank 36 by line 35 at a rate of 100 parts per hour. The oxidizer product had an average composition of 85% acetic acid and 15% water. The overall yield of acetic acid based on the EDA fed via line 17 to the hydrolysis zone ranges from 90 to 100%.

The process of the present invention is further illustrated by the following examples wherein percentages are by weight and pressure is given in bars absolute.

HYDROLYSIS

The hydrolysis zone consisted of a 500 mL, 3-neck flask hydrolysis vessel equipped with a stirrer, thermometer and 2 sub-surface feed lines and connected to an entrainment separator consisting of a 5-plate Oldershaw column. In each example, acetic acid (200 g) and methanesulfonic acid (1 g) were charged to the flask and heated to boiling (113° to 130° C.) prior to the commencement of the feeds of the EDA and water streams.

EXAMPLE 1

An EDA stream consisting of 89.2% EDA, 2% acetic anhydride, 9% acetic acid 15 ppm iodine and obtained from the procedure described in Example 5 is fed below the surface of the boiling acetic acid at a rate of 456 g per hour. Water also is fed sub-surface at a rate of 70 g per hour. A vapor product consisting of 22% acetaldehyde, 73% acetic acid, 5% water and 12 ppm iodine was removed from the entrainment separator at a rate of 526 g per hour. Analysis of the overhead product shows 100% hydrolysis of the EDA to acetaldehyde and acetic acid.

EXAMPLE 2

Example 1 is repeated except that the EDA feed containing 36 ppm iodine is provided by the iodine removal procedure of Example 6. The overhead vapor product consists of 24% acetaldehyde, 70% acetic acid, 6% water and 29 ppm iodine.

EXAMPLE 3

Example 1 is repeated except that the EDA feed material contains 740 ppm iodine and is not subjected to an iodine removal step prior to hydrolysis. The overhead vapor product consists of 24% acetaldehyde, 70% acetic acid, 6% water and 363 ppm iodine.

OXIDATION

The oxidation zone consisted of a vertical, glass tube oxidizer 60 inches (152.4 cm) in length and 2 inches (5.1 cm) in diameter having a capacity of 3.7L and equipped with inlets at the base for feeding air and the hydrolysis zone effluent. The top of the oxidizer was equipped with, in order, a heater exchanger for condensing acetic acid and water from the oxidizer vapor effluent, a vapor/liquid separator, a pressure-regulating valve, a trap cooled to $-67°$ C. by dry ice (solid carbon dioxide) and a scrubber. The oxidizer is charged initially with an acetic acid solution containing 5 weight percent water and 0.3 weight percent cobalt, provided as cobalt hydrate or cobalt acetate. The oxidizer is heated to 130° C. by means of an electric heating cable and pressurized with air which was sparged to the bottom of the oxidation vessel while feeding either acetaldehyde or the EDA hydrolysis product.

EXAMPLE 4

The EDA hydrolysis product from Example 3 is fed to the oxidizer at a rate of 110 mL per hour and oxidized at steady state conditions of 130° C. and 3.08 bars. The feed rate of the EDA hydrolysis product and the vapor product take-off rate are regulated to maintain a constant liquid level (expanded) in the oxidizer of approximately 3L. The acetic acid/water mixture collected from the vapor/liquid separator contains 36 ppm iodine and the liquid collected in the dry ice trap has an iodine content of 755 ppm iodine.

IODINE REMOVAL

The iodine removal vessel consisted of a 500 mL, 3-neck flask equipped with a stirrer, thermometer, 2 sub-surface feed lines and an overflow line and connected to a 3-inch Vigreaux column. Each example was commenced with a 200 mL charge of EDA to the flask.

EXAMPLE 5

An EDA stream consisting of 88.2% EDA, 7% acetic anhydride, 3% acetic acid and 140 ppm iodine and 35% aqueous hydrogen peroxide solution are fed sub-surface to the iodine removal vessel at rates of 363 g per hour and 10 g per hour, respectively. A vapor effluent consisting of 45.5% water, 36.4% acetic acid, 18.1% EDA and 300 ppm iodine is removed from the Vigreaux column at a rate of 11 g per hour. A liquid effluent consisting of 89% EDA, 2% acetic anhydride, 9% acetic acid and 15 ppm iodine is removed from the flask via the overflow line at a rate of 362 g per hour.

EXAMPLE 6

The procedure described in Example 5 is repeated except that the EDA feed material contains 740 ppm iodine (as iodoacetic acid) and the rate of feed of 35% aqueous hydrogen peroxide solution is 15 g per hour. The vapor effluent contains 1197 ppm iodine (as methyl iodide) and the liquid effluent contains 36 ppm iodine (as iodoacetic acid).

EXAMPLE 7

The procedure described in Example 5 is repeated except that the EDA feed material contains 1144 ppm iodine and the rate of feed of 35% aqueous hydrogen peroxide solution is 23 g per hour. The vapor effluent contains 2648 ppm iodine and the liquid effluent contains 64 ppm iodine.

The invention has been described in detail with particular reference to preferred embodiments thereof, but it will be understood that variations and modifications can be effected within the spirit and scope of the invention.

We claim:

1. Process for the recovery of acetyl values from ethylidene diacetate which comprises the steps of:
   (1) feeding ethylidene diacetate and water to a liquid phase, hydrolysis zone containing a non-volatile, acidic catalyst and maintained under boiling conditions;
   (2) removing from the hydrolysis zone a vapor comprising acetaldehyde, acetic acid and water;
   (3) feeding the acetaldehyde, acetic acid and water from step (2) to a liquid phase, oxidation zone containing a cobalt oxidation catalyst; and
   (4) removing from the oxidation zone a vapor comprising acetic acid and water.

2. Process according to claim 1 which comprises the steps of:
   (1) feeding ethylidene diacetate and water to a liquid phase, hydrolysis zone containing 0.5 to 10 weight percent of an alkylsulfonic acid catalyst and maintained under boiling conditions, wherein the water-:ethylidene diacetate male feed rates are at least 1:1,
   (2) removing from the hydrolysis zone a vapor comprising acetaldehyde, acetic acid and water;
   (3) feeding the acetaldehyde, acetic acid and water from step (2) to a liquid phase, oxidation zone containing a cobalt oxidation catalyst and maintained at a temperature of about 100° to 130° C. and a pressure of about 2.4 to 4.5 bars absolute; and
   (4) removing from the oxidation zone a vapor comprising acetic acid and water.

3. Process for the recovery of acetyl values from ethylidene diacetate which comprises the steps of:
   (1) feeding ethylidene diacetate and water to a liquid phase, hydrolysis zone containing 0.3 to 1 weight percent of methanesulfonic acid catalyst and maintained under boiling conditions, wherein the water-:ethylidene diacetate male feed rates are about 1.2:1 to 1.5:1;
   (2) removing from the hydrolysis zone a vapor comprising acetaldehyde, acetic acid and water;
   (3) feeding the acetaldehyde, acetic acid and water from step (2) to a liquid phase, oxidation zone containing about 0.18 to 5 weight percent of a cobalt oxidation catalyst and maintained at a temperature of about 100° to 130° C. and a pressure of about 2.4 to 4.5 bars absolute; and
   (4) removing from the oxidation zone a vapor comprising acetic acid and water.

4. Process according to claim 1 wherein the ethylidene diacetate feed of step (1) is obtained from an iodine removal process comprising the steps of:
   (i) contacting in a purification zone a mixture comprising ethylidene diacetate, acetic anhydride, acetic acid and at least 100 ppm iodine with aqueous hydrogen peroxide at a temperature of 140° to 160° C.; and
(ii) removing from the purification zone
(a) a vapor phase comprising water, acetic acid and iodine-containing compounds; and
(b) a liquid phase comprising ethylidene diacetate containing less than about 100 ppm iodine.

5. Process for the recovery of acetyl values from ethylidene diacetate which comprises the steps of:
(1) feeding ethylidene diacetate and water to a liquid phase, hydrolysis zone containing 0.5 to 10 weight percent of an alkylsulfonic acid catalyst and maintained under boiling conditions, wherein the water::ethylidene diacetate male feed rates are at least 1:1;
(2) removing from the hydrolysis zone a vapor comprising acetaldehyde, acetic acid and water;
(3) feeding the acetaldehyde, acetic acid and water from step (2) to a liquid phase, oxidation zone containing a cobalt oxidation catalyst and maintained at a temperature of about 100° to 130° C. and a pressure of about 2.4 to 4.5 bars absolute; and
(4) removing from the oxidation zone a vapor comprising acetic acid and water;
wherein the ethylidene diacetate feed of step (1) is obtained from an iodine removal process comprising the steps of:
(i) contacting in a purification zone a mixture comprising ethylidene diacetate, acetic anhydride, acetic acid and about 100 to 1500 ppm iodine with about 3 to 6 weight percent, based on the weight of the mixture, of 30 to 70 weight percent aqueous hydrogen peroxide at a temperature of 140° to 160° C.; and
(ii) removing from the purification zone
(a) a vapor phase comprising water, acetic acid and iodine-containing compounds; and
(b) a liquid phase comprising ethylidene diacetate containing less than about 100 ppm iodine.

* * * * *

UNITED STATES PATENT AND TRADEMARK OFFICE
CERTIFICATE OF CORRECTION

PATENT NO. : 5,175,362
DATED : December 29, 1992
INVENTOR(S) : Carl F. Fillers et al.

It is certified that error appears in the above-identified patent and that said Letters Patent is hereby corrected as shown below:

Column 8, line 36 (Claim 2, line 7) "male" should be --- mole ---.

Column 8, line 52 (Claim 3, line 7) "male" should be --- mole ---.

Column 9, line 15 (Claim 5, line 7) "male" should be --- mole ---.

Signed and Sealed this

Nineteenth Day of October, 1993

Attest:

BRUCE LEHMAN

*Attesting Officer*    *Commissioner of Patents and Trademarks*